United States Patent
Fielden et al.

(10) Patent No.: US 11,085,980 B2
(45) Date of Patent: Aug. 10, 2021

(54) DETECTING SIGNAL CHANGES IN HEATED BONE WITH A 3D SPIRAL ULTRA-SHORT ECHO TIME SEQUENCE

(71) Applicants: UNIVERSITY OF VIRGINIA PATENT FOUNDATION, Charlottesville, VA (US); The Board of Trustees of the Leland Stanford Junior University, Stanford, CA (US)

(72) Inventors: Samuel W. Fielden, Lewisburg, PA (US); John P. Mugler, III, Charlottesville, VA (US); G. Wilson Miller, IV, Charlottesville, VA (US); Kim Butts Pauly, Stanford, CA (US); Craig H. Meyer, Charlottesville, VA (US)

(73) Assignees: University of Virginia Patent Foundation, Charlottesville, VA (US); The Board of Trustees of the Leland Stanford Junior University, Stanford, CA (US)

( * ) Notice: Subject to any disclaimer, the term of this patent is extended or adjusted under 35 U.S.C. 154(b) by 1007 days.

(21) Appl. No.: 15/593,894

(22) Filed: May 12, 2017

(65) Prior Publication Data
US 2017/0328972 A1 Nov. 16, 2017

Related U.S. Application Data

(60) Provisional application No. 62/335,372, filed on May 12, 2016.

(51) Int. Cl.
*G01R 33/50* (2006.01)
*G01R 33/48* (2006.01)
(Continued)

(52) U.S. Cl.
CPC ............. *G01R 33/50* (2013.01); *A61B 90/37* (2016.02); *A61N 7/02* (2013.01); *G01R 33/4816* (2013.01);
(Continued)

(58) Field of Classification Search
CPC G01R 33/50; G01R 33/4816; G01R 33/4804; G01R 33/4826; A61B 90/37;
(Continued)

(56) References Cited

U.S. PATENT DOCUMENTS

| | | | |
|---|---|---|---|
| 8,386,013 B2* | 2/2013 | Du Jiang et al. | A61B 5/05 600/410 |
| 2015/0282733 A1* | 10/2015 | Fielden | A61B 5/725 600/411 |
| 2016/0008633 A1* | 1/2016 | Vortman et al. | A61N 7/00 |

OTHER PUBLICATIONS

Han et al. 2015 Journal of Therapeutic Ultrasound 3 (Suppl. 1):P5 2 pages (Year: 2015).*

(Continued)

*Primary Examiner* — Michael J Tsai
*Assistant Examiner* — Patrick M Mehl
(74) *Attorney, Agent, or Firm* — Meunier Carlin & Curfman LLC

(57) ABSTRACT

In one aspect, in accordance with one embodiment, a method includes acquiring magnetic resonance (MR) data corresponding to bone tissue in an area of interest of a subject that is heated from the application of localized energy. The acquiring includes applying a three-dimensional (3D) ultra-short echo time (UTE) spiral acquisition sequence. The method also includes detecting, from the acquired magnetic resonance data, a change in MR response signal due to a change in at least one of relaxation rate and magnetization density caused by heating of the bone tissue; and determining, based at least in part on the change in the (Continued)

MR response signal, that the temperature of the bone tissue has changed.

20 Claims, 11 Drawing Sheets
(6 of 11 Drawing Sheet(s) Filed in Color)

(51) Int. Cl.
| | | |
|---|---|---|
| *A61B 5/055* | (2006.01) | |
| *A61B 5/01* | (2006.01) | |
| *A61N 7/00* | (2006.01) | |
| *A61N 7/02* | (2006.01) | |
| *A61B 90/00* | (2016.01) | |

(52) U.S. Cl.
CPC ............... *A61B 5/01* (2013.01); *A61B 5/055* (2013.01); *A61B 2090/374* (2016.02); *A61N 2007/0078* (2013.01); *A61N 2007/0082* (2013.01); *A61N 2007/0095* (2013.01); *G01R 33/4804* (2013.01); *G01R 33/4826* (2013.01)

(58) Field of Classification Search
CPC ..... A61B 2090/374; A61B 5/01; A61B 5/055; A61N 7/02; A61N 2007/0078; A61N 2007/0095; A61N 2007/0082; A61N 7/00; A61N 2005/1055
See application file for complete search history.

(56) References Cited

OTHER PUBLICATIONS

Du et al. 2010 Journal of Magnetic Resonance 207:304-311 (Year: 2010).*

Qian et al. 2012 eMagRes. 1:737-746; https://onlinelibrary.wiley.com/doi/full/10.1002/9780470034590.emrstm1297 (Year: 2012).*

Wilson Miller, Toward T1-Based Thermometry in Cortical Bone Using Ultrashort Echo-Time MRI, 3rd International Symposium on Focused Ultrasound, p65-BN, (2012)1 page.

Yongxian Qian and Fernando E. Boada, Acquisition-Weighted Stack of Spirals for Fast High-Resolution Three-Dimensional Ultrashort Echo Time MR Imaging, Magnetic Resonance in Medicine 60:135-145 (2008).

Rieke, V. and Pauly, K., MR Thermometry, Journal of Magnetic Resonance Imaging 27:376-390 (2008).

Peder Eric Zufall Larson, Misung Han, Sarah J. Nelson, Daniel B. Vigneron, Roland Krug, and Douglas A. C. Kelley. In vivo Comparison of Ultrashort Echo Time (UTE) and Zero Echo Time (ZTE) MRI at 7T. Abstract #0816. Joint Annual Meeting ISMRM-ESMRMB Milan, Italy 2014.

* cited by examiner

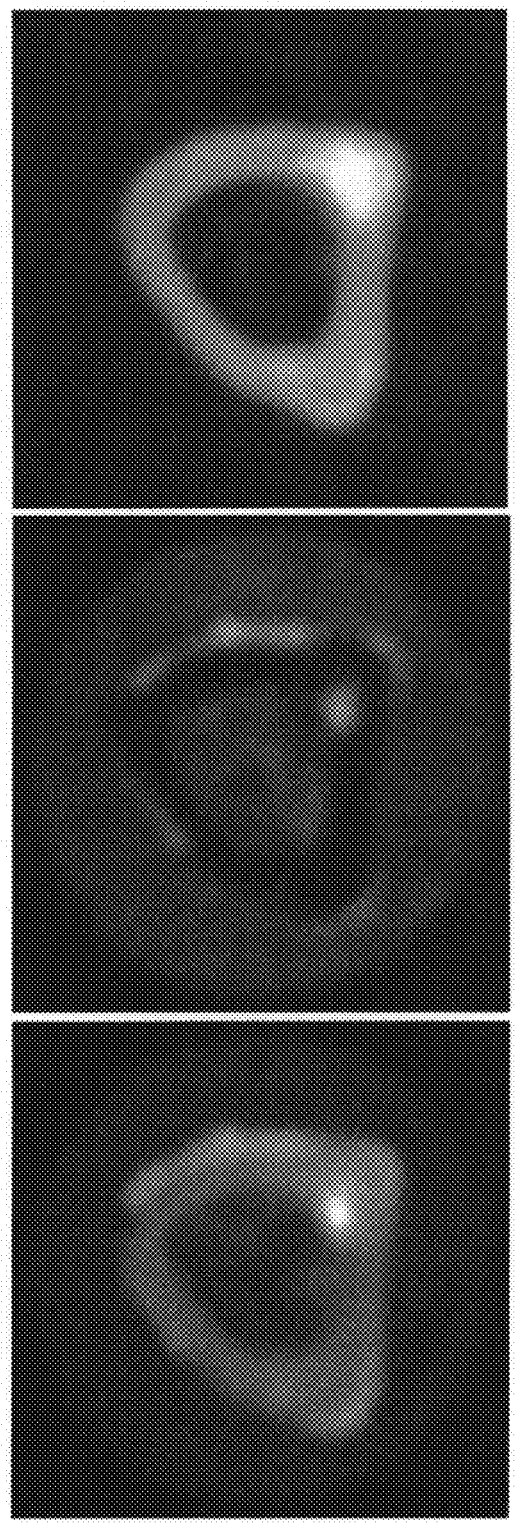
FIG. 6A min TE
FIG. 6B late TE
FIG. 6C subtraction

DETECTING SIGNAL CHANGES IN HEATED BONE WITH A 3D SPIRAL ULTRA-SHORT ECHO TIME SEQUENCE

CROSS-REFERENCE TO RELATED APPLICATION

This application claims priority to and benefit of U.S. Provisional Patent Application No. 62/335,372, filed May 12, 2016, which is hereby incorporated by reference herein in its entirety as if fully set forth below.

BACKGROUND

Magnetic resonance (MR) based thermal therapies, such as MRI-guided focused ultrasound (FUS) treatment, are proven technologies for non-invasive surgical procedures. MRI-guided FUS can be particularly suited for non-invasive tissue ablation in regions where internal organs and tissues are easily imaged and monitored for temperature. Soft tissues can be readily imaged with conventional MRI sequences that employ relatively long echo times. Temperatures in the soft tissues may be monitored by exploiting the temperature dependence of the proton resonant frequency (PRF) in water. Due to its short T2/T2*, temperature monitoring using the PRF technique cannot be performed for bone tissues, however. Because cortical bone is dense and poorly vascularized, heat dissipates slowly and can reach dangerous levels if ultrasound sonications are performed too frequently.

It is with respect to these and other considerations that the various embodiments described below are presented.

SUMMARY

In some aspects, the present disclosure relates to systems and methods for detecting MR signal changes due to change in temperature of an area of interest of a subject, using a three-dimensional (3D) spiral ultrashort echo time (UTE) sequence. In some aspects, the present disclosure also relates to monitoring temperature characteristics of bone tissue that has been heated from the application of localized energy, using magnetic resonance imaging (MRI) techniques and based on detecting changes in the MR response signal.

In one aspect, the present disclosure relates to a method which, in one embodiment, includes acquiring magnetic resonance (MR) data corresponding to bone tissue in an area of interest of a subject that is heated from the application of localized energy. The acquiring comprises applying a three-dimensional (3D) ultra-short echo time (UTE) spiral acquisition sequence. The method also includes detecting, from the acquired magnetic resonance data, a change in MR response signal due to a change in at least one of relaxation rate and magnetization density caused by heating of the bone tissue, and determining, based at least in part on the change in the MR response signal, that the temperature of the bone tissue has changed.

In another aspect, the present disclosure relates to a system which, in one embodiment, includes a data acquisition device configured to acquire magnetic resonance (MR) data corresponding to bone tissue in an area of interest of a subject that is heated from the application of localized energy. The acquiring includes applying a three-dimensional (3D) ultra-short echo time (UTE) spiral acquisition sequence. The system also includes one or more processors coupled to the data acquisition device and configured to cause the system to perform functions that include: detecting, from the acquired magnetic resonance data, a change in MR response signal due to a change in at least one of relaxation rate and magnetization density caused by heating of the bone tissue; and determining, based at least in part on the change in the MR response signal, that the temperature of the bone tissue has changed.

In another aspect, the present disclosure relates to a non-transitory computer-readable medium having stored instructions that, when executed by one or more processors, cause one or more computing devices to perform specific functions. In one embodiment, the specific functions performed include acquiring magnetic resonance (MR) data corresponding to bone tissue in an area of interest of a subject that is heated from the application of localized energy. The acquiring includes applying a three-dimensional (3D) ultra-short echo time (UTE) spiral acquisition sequence. The specific functions performed also include detecting, from the acquired magnetic resonance data, a change in MR response signal due to a change in at least one of relaxation rate and magnetization density caused by heating of the bone tissue. The specific functions performed also include determining, based at least in part on the change in the MR response signal, that the temperature of the bone tissue has changed.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale. The patent or application file contains at least one drawing executed in color. Copies of this patent or patent application publication with color drawing(s) will be provided by the Office upon request and payment of the necessary fee.

FIG. 6A-6C show spiral UTE images of a bone sample, obtained by implementing aspects of the present disclosure in accordance with some embodiments.

DETAILED DESCRIPTION

Figure 1:
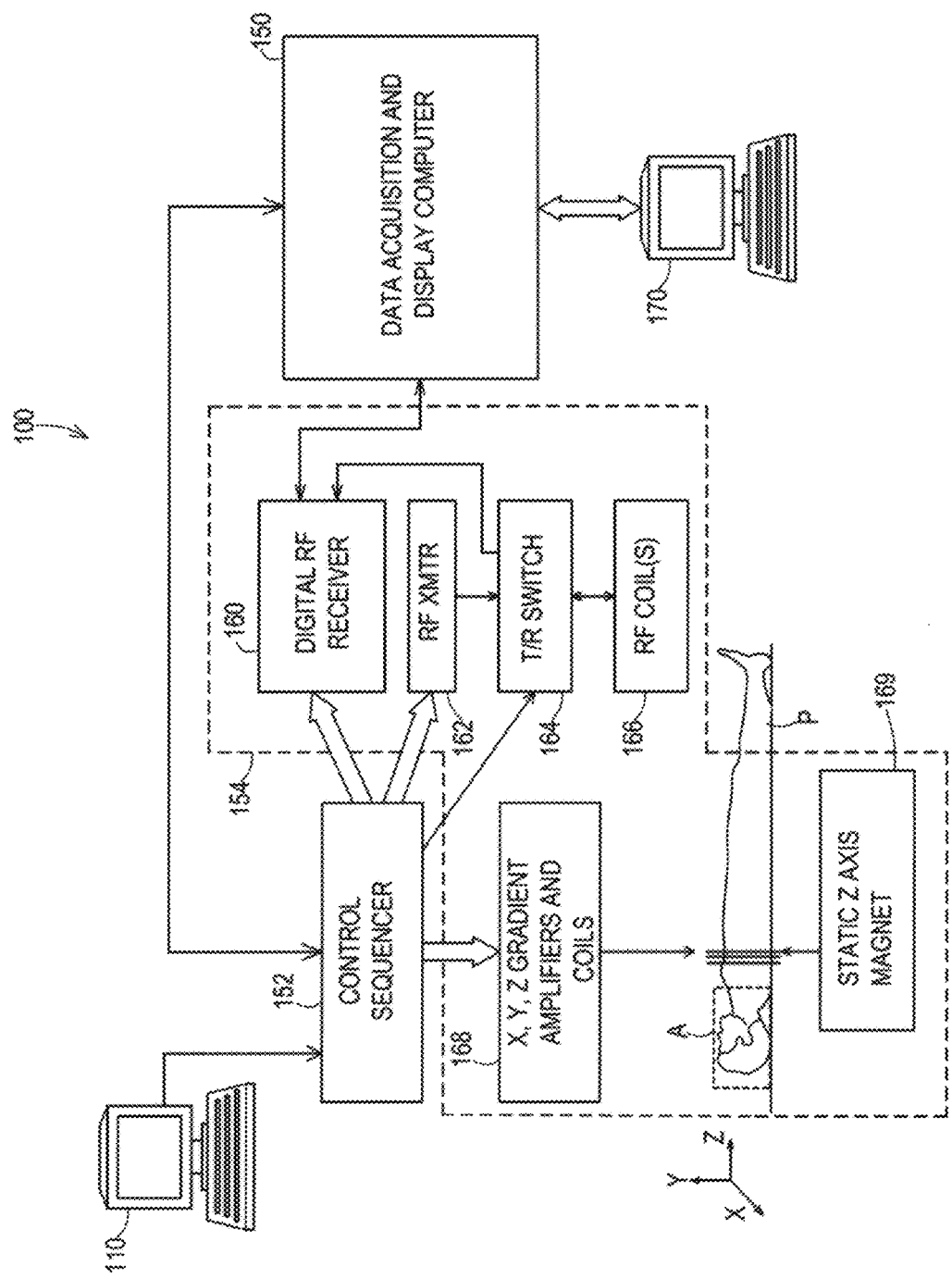
FIG. 1 is a system diagram illustrating an imaging system capable of implementing aspects of the present disclosure in accordance with one or more embodiments.

Systems and methods disclosed herein in accordance with some embodiments can utilize a 3D spiral-based UTE sequence to rapidly collect UTE images and detect signal changes in certain tissues, for example in cortical bone tissue as it changes temperature when inside the bore of an MRI system. The change in temperature can be due to heating caused by the application of localized energy, such as from the application of focused ultrasound (FUS), laser radiation, or RF signals, among other possible sources. Systems and methods disclosed herein in accordance with some embodiments can utilize MRI to directly monitor bone heating during FUS treatment.

A number of MR parameters show a sensitivity to temperature, including T1 and T2 relaxation rates and proton density. For example, T1 relaxation rates increase for certain tissues, including bone tissues, when the temperature of the tissue increases, and the MR response signal can show an associated decrease in signal level/intensity. By detecting changes in the signal that are attributable to the change in relaxation rate(s) and/or magnetization density (e.g., proton density) caused by the temperature change for the tissue, it can be determined whether a change in temperature has occurred. Further, temperature and/or changes in temperature of the tissue can be determined. For determining that a change in temperature of the tissue has occurred, and/or for measuring the temperature and/or change in temperature, the signal may be compared to a reference signal corresponding to a known temperature, for example a reference signal corresponding to the tissue when it is not heated (e.g., when at room temperature or when not being subjected to localized energy).

With regard to magnetization density, proton density depends linearly on the equilibrium magnetization, which is determined by the Boltzman distribution. (See, e.g., Rieke, V. and Pauly, K., MR Thermometry, Journal of Magnetic Resonance Imaging 27:376-390 (2008) ("Reike et al."). Because the equilibrium magnetization depends on the Boltzmann thermal equilibrium, temperature changes can be evaluated based on proton density-weighted images. (See, e.g., Rieke et al.).

Practicing aspects of the present disclosure in accordance with various embodiments can provide for temperature monitoring of bone across potentially large fields of view. Volumetric UTE sequences have typically required long scan times, precluding their use in focused ultrasound procedures. However, 3D spiral UTE sequence and implementations thereof in accordance with embodiments described herein can rapidly acquire large amounts of volumetric data within short periods of time and within short enough time frames that changes in the MR response signal due to changes in T1 and/or T2 relaxation rates can be detected. The changes in response signal can be correlated to temperature characteristics of the bone, for example temperature of the bone or change in temperature of the bone.

Among other advantageous implementations, some embodiments of the present disclosure allow for a large area of interest to be monitored to determine when it is safe to apply focused energy, such that the tissue temperature does not enter unsafe levels. For example, as will be described below in further detail, a 3D spiral UTE sequence in accordance with some embodiments of the present disclosure can rapidly image the entire skull and skull base between therapeutic sonications, which are typically separated by a few minutes. As mentioned above, for certain brain procedures, ultrasound waves pass through the skull and deposit a large amount of energy in the bone, resulting in bone heating, and because cortical bone is dense and poorly vascularized, heat dissipates slowly and can reach dangerous levels if sonications are performed too frequently. Certain embodiments of the present disclosure described herein can be implemented for monitoring off-target heating of the skull when applying localized energy, or to directly monitor bone heating when applying localized energy in or near the bone, such as when treating bone metastases using focused ultrasound.

Other aspects and features according to the present disclosure will become apparent to those of ordinary skill in the art, upon reviewing the following detailed description in conjunction with the accompanying figures.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise.

Certain values and/or ranges may be expressed in terms of "about" or "approximately" a value or range. For example, a range may be from "about" or "approximately" one particular value to "about" or "approximately" another particular value. When such a range is expressed, other exemplary embodiments include from the one particular value and/or to the other particular value. As used herein, "about" means within 20 percent or closer of a given value or range.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" or "patient" may be any applicable human, animal, or other organism, living or dead, or other biological or molecular structure or chemical environment, and may relate to particular components of the subject, for instance specific organs, bones, tissues, or fluids, which may be in a particular location of the subject referred to herein as an "area of interest" or a "region of interest."

Some references, which may include various patents, patent applications, and publications, may be cited and/or discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference.

A detailed description of aspects of the present disclosure will now be provided with reference to the accompanying drawings. The drawings form a part hereof and show, by way of illustration, specific embodiments or examples. In referring to the drawings, like numerals represent like elements throughout the several figures.

FIG. 1 is a system diagram illustrating an imaging system capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged, for example to implement magnetic resonance imaging sequences in accordance with various embodiments of the present disclosure. Reconstructed images, such as contrast-enhanced image(s) of an area of interest A of the subject P may be shown on display 170.

The area of interest A shown in the example embodiment of FIG. 1 corresponds to a head region of subject P, but it should be appreciated that the area of interest for purposes of implementing various aspects of the disclosure presented herein is not limited to the head area. It should be recognized and appreciated that the area of interest in various embodiments may encompass various areas of subject P associated with various physiological characteristics, such as, but not limited to the head and brain region, chest region, heart region, abdomen, upper or lower extremities, or other organs or tissues. Various aspects of the present disclosure are described herein as being implemented on portions of the skeletal system of human subjects, for example cortical bone tissue.

It should be appreciated that any number and type of computer-based medical imaging systems or components, including various types of commercially available medical imaging systems and components, may be used to practice certain aspects of the present disclosure. Systems as described herein with respect to imaging are not intended to be specifically limited to the particular system shown in FIG. 1. Likewise, systems as described herein with respect to the application of localized energy for heating certain areas for thermal treatment are not intended to be specifically limited to the particular systems shown in FIG. 2A or 2B described below.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2A:
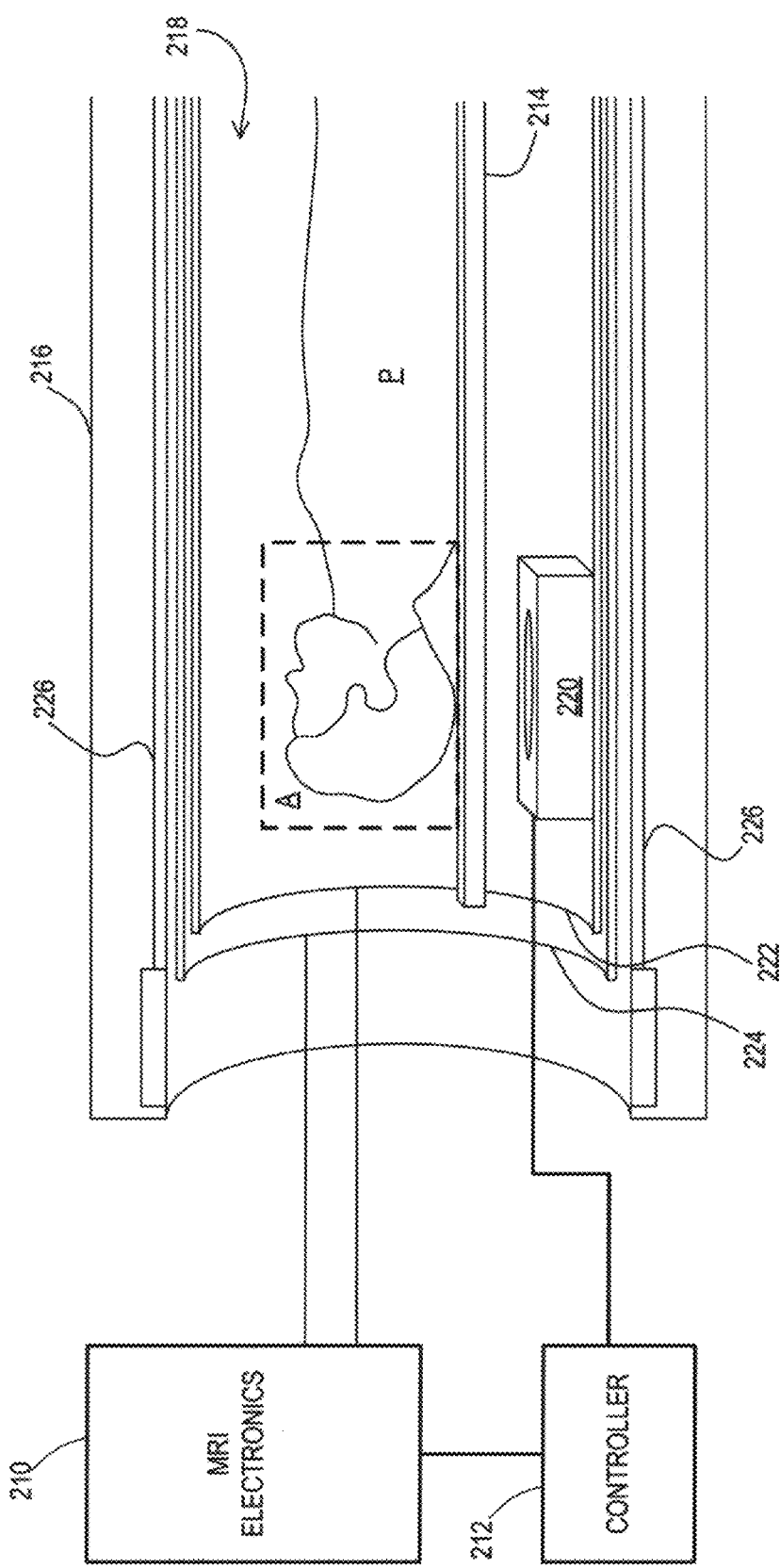
FIG. 2A is a diagram showing one example embodiment of a system with thermal therapy used with MRI, which is capable of implementing aspects of the present disclosure in accordance with one or more embodiments.
Figure 2B:
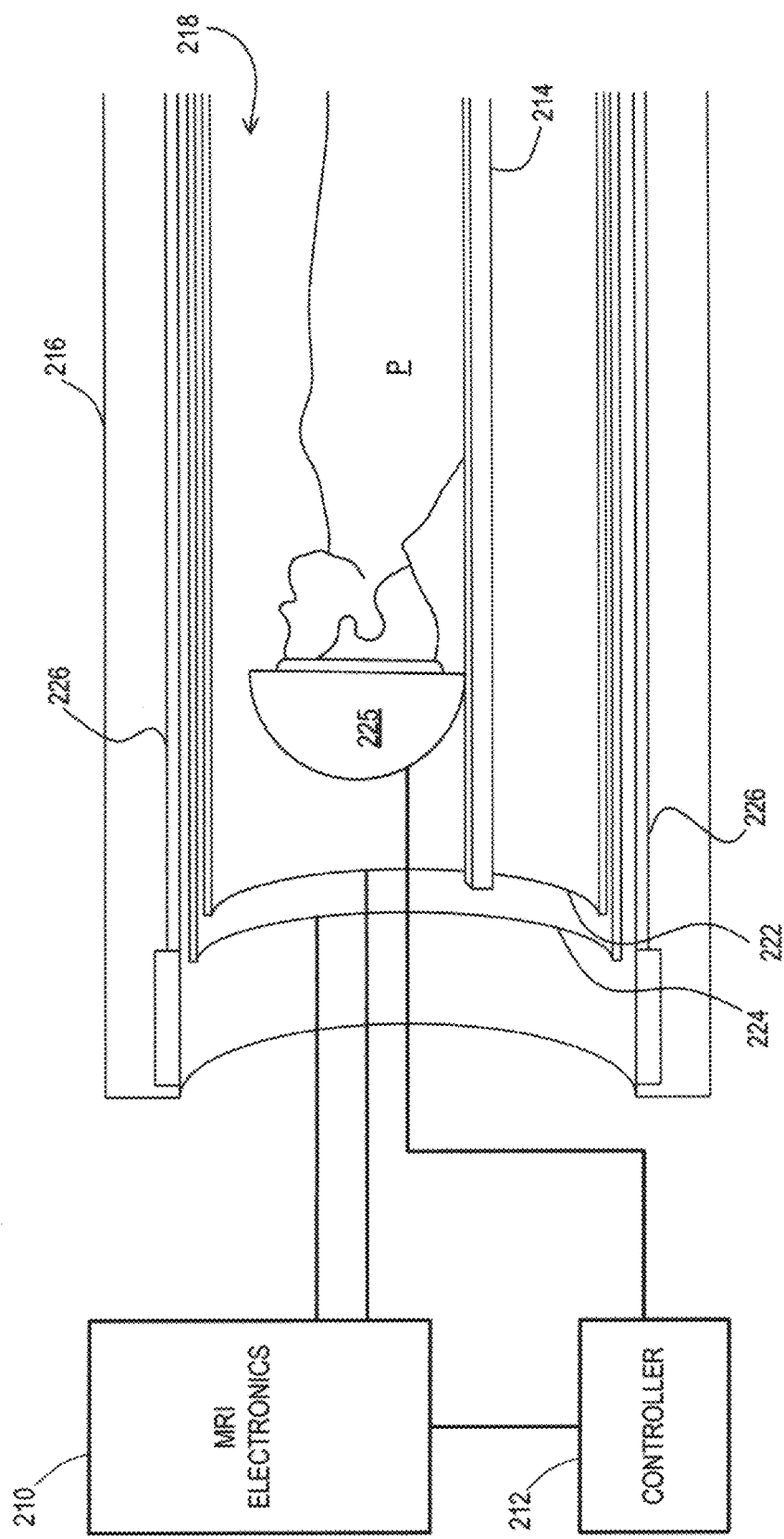
FIG. 2B is a diagram showing another example embodiment of a system with thermal therapy used with MRI, which is capable of implementing aspects of the present disclosure in accordance with one or more embodiments.

FIG. 2A and FIG. 2B are diagrams showing two respective embodiments of systems with focused ultrasound (FUS) used with MRI, each of which is capable of implementing aspects of the present disclosure in accordance with one or more embodiments. FIG. 2A shows a first type of FUS device 220 used in combination with MRI. The MRI system may comprise one or more components of the system 100 shown in FIG. 1. As shown, RF coils 222, gradient coils 224, static Z axis magnet 226, and magnetic housing 216 surround the patient P when the patient is positioned on the table 214 inside of the MRI bore 218. A controller 212 communicates with MRI system electronics 210 as well as the FUS device (220 in FIG. 2A, 225 in FIG. 2B). The MRI system electronics 210 can include one or more components of the MRI subsystem 154 shown in FIG. 1. A user computer (not shown) may communicate with the controller 212 for control of the MRI system and FUS device functions. As shown in the embodiment of FIG. 2A, a first type of FUS device 220 is disposed under the head of the patient P and within the bore 218 such that focused ultrasound energy may be applied to target the area of interest A. As one example, the device 220 can be an Insightec Exablate focused ultrasound device.

In FIG. 2B, a second type of FUS device 225 surrounds the patient's head, as may be used for thermal therapy applied to tissues of or near the brain. The device 225 may have multiple ultrasound transducers for applying focused energy to particular target areas of interest of the head of the patient. As one example, the device 225 may be an Insightec Exablate Neuro focused ultrasound device.

The devices 220 and/or 225 can be configured to apply localized energy to heat a targeted region within the area of interest A which includes tissues of or near the brain. As a result, heating may occur in bone tissues, such as that of the skull. The MRI components of the system (including MRI electronics 210) are configured to work within a larger MRI system to acquire magnetic resonance data and for reconstructing images of all or regions of the area of interest as well as temperature-related data. The temperature data may include a temperature at a targeted region and/or a temperature at a reference region. The temperature data may be used to monitor the effectiveness and safety of the thermal therapy treatment and adjust treatment settings accordingly.

The targeted region may include bone tissue, which as described above, has a short $T2/T2^*$. Control of the application of the focused energy via the controller 212 may be managed by an operator using an operator console (e.g., user computer). The controller 212 (which, as shown is also coupled to MRI electronics 210) may also be configured to manage functions for the application and/or receiving of MR signals. For example, the controller 212 may be coupled to a control sequencer such as the control sequencer 152 shown in FIG. 1.

Although the FUS devices 220, 225 shown in the embodiments of FIG. 2A and FIG. 2B utilize ultrasound transducer(s) as the source for delivering localized energy to an area of interest, it should be appreciated that other types of devices may alternatively be used without departing from the patentable scope of the present disclosure. Other possible types of thermal treatment/application devices that may be utilized include laser and/or RF ablation devices, or other devices adapted to heat a target tissue.

Figure 3:
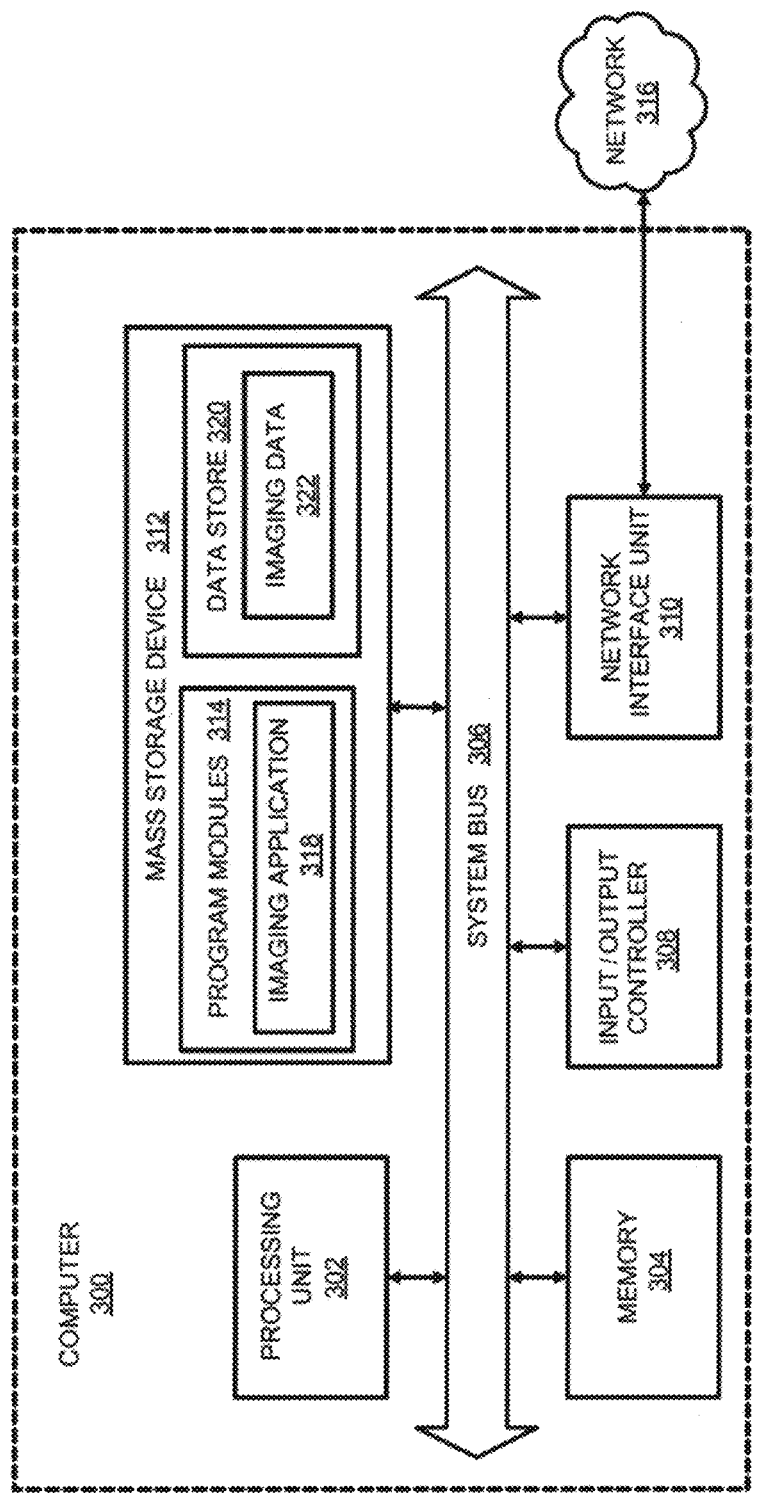
FIG. 3 is a computer architecture diagram showing a computing system capable of implementing aspects of the present disclosure in accordance with one or more embodiments.

FIG. 3 is a computer architecture diagram showing a computing system capable of implementing aspects of the present disclosure in accordance with one or more embodiments described herein. A computer 300 may be configured to perform one or more specific steps of a method and/or specific functions for a system. The computer may be configured to perform one or more functions associated with embodiments illustrated in one or more of FIGS. 4-10. For example, the computer 300 may be configured to perform aspects described herein for implementing the pulse sequence shown in FIG. 4 and for various aspects of magnetic resonance imaging and related signal and temperature monitoring shown in FIGS. 5-10. It should be appreciated that the computer 300 may be implemented within a single computing device or a computing system formed with multiple connected computing devices. The computer 300 may be configured to perform various distributed computing tasks, in which processing and/or storage resources may be distributed among the multiple devices. The data acquisition and display computer 150 and/or operator console 110 of the system shown in FIG. 1, and the controller 212 and/or MRI electronics 210 of the system shown in FIG. 2, may include one or more components of the computer 300.

As shown, the computer 300 includes a processing unit 302 ("CPU"), a system memory 304, and a system bus 306 that couples the memory 304 to the CPU 302. The computer 300 further includes a mass storage device 312 for storing program modules 314. The program modules 314 may be operable to perform functions associated with one or more embodiments described herein. For example, when executed, the program modules can cause one or more medical imaging devices, localized energy producing devices, and/or computers to perform functions described herein for implementing the pulse sequence shown in FIG. 4, the method shown in FIG. 5, and for various aspects of magnetic resonance imaging and related signal and temperature monitoring and analysis shown in FIGS. 5-10. The program modules 314 may include an imaging application 318 for performing data acquisition and/or processing functions as described herein, for example to acquire and/or process image data corresponding to magnetic resonance imaging of an area of interest. The computer 300 can include a data store 320 for storing data that may include imaging-related data 322 such as acquired data from the implementation of magnetic resonance imaging pulse sequences in accordance with various embodiments of the present disclosure.

The mass storage device 312 is connected to the CPU 302 through a mass storage controller (not shown) connected to the bus 306. The mass storage device 312 and its associated computer-storage media provide non-volatile storage for the computer 300. Although the description of computer-storage media contained herein refers to a mass storage device, such as a hard disk, it should be appreciated by those skilled in the art that computer-storage media can be any available computer storage media that can be accessed by the computer 300.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 300. "Computer storage media", "computer-readable storage medium" or "computer-readable storage media" as described herein do not include transitory signals.

According to various embodiments, the computer 300 may operate in a networked environment using connections to other local or remote computers through a network 316 via a network interface unit 310 connected to the bus 306. The network interface unit 310 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems.

The computer 300 may also include an input/output controller 308 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 300. The input/output controller 308 may be configured to manage output to one or more display devices for displaying visually representations of data, such as display monitors/screens that are integral with other components of the computer 300 or are remote displays.

The bus 306 may enable the processing unit 302 to read code and/or data to/from the mass storage device 312 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state, or may include rotating media storing magnetically-encoded information. The program modules 314, which include the imaging application 318, may include instructions that, when loaded into the processing unit 302 and executed, cause the computer 300 to provide functions associated with one or more embodiments illustrated in FIGS. 4-10. The program modules 314 may also provide various tools or techniques by which the computer 300 may participate within the overall systems or operating environments using the components, flows, and data structures discussed throughout this description.

FIGS. 4A and 4B show aspects of variable-TE 3D spiral pulse sequence in accordance with some embodiments of the present disclosure. As shown, from the excitation event, transverse decay advances rapidly for short T2 species. In some embodiments, each partition is sampled at a different time delay from the RF pulse, and so has a different echo time. The amount of transverse decay that has occurred when each partition is encoded impacts the amplitude of the resulting signal. As such, the signal intensity is a function of echo time, and it directly follows that the signal intensity changes as a function of k-space partition number. Very short TEs are achievable near the center of k-space, where the through-plane PE gradients are small or nonexistent. In some embodiments, a 3D spoiled gradient-echo sequence (VIBE, Siemens) is modified to support the stack-of-spirals acquisition, to make room for spiral gradients instead of standard Cartesian readout events, by using a fast, nonselective pulse for excitation and varying the TE depending on the partition-encoding gradient.

Figure 4:
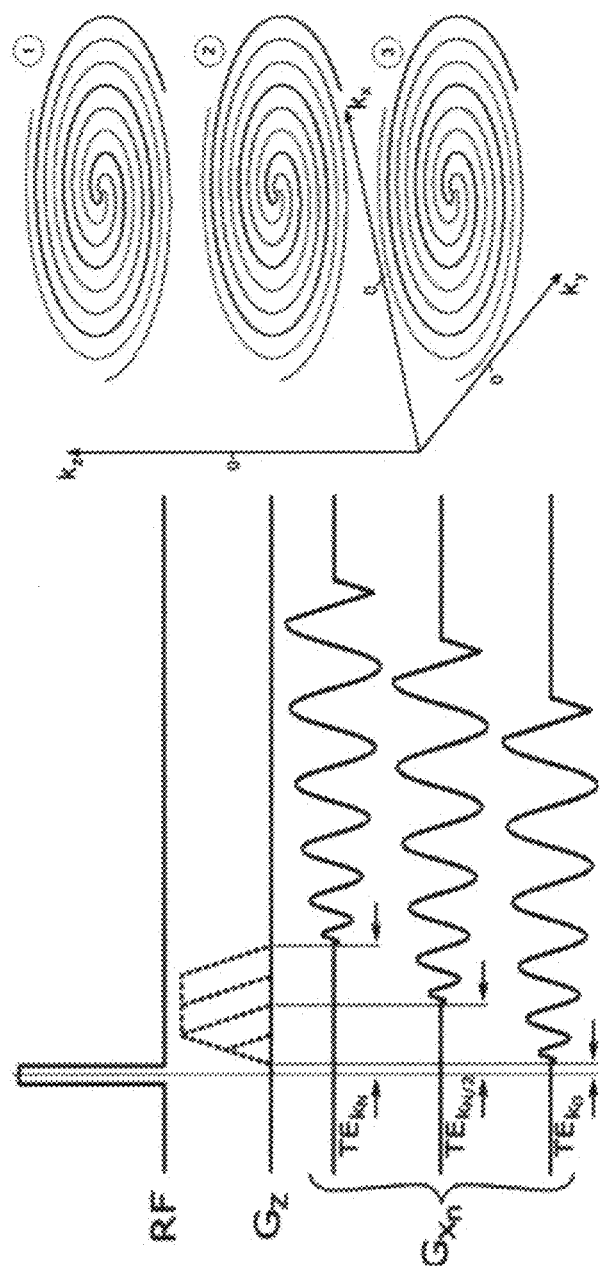
FIGS. 4A and 4B illustrate a variable-TE 3D spiral pulse sequence and spiral interleaves, respectively, in accordance with some embodiments of the present disclosure.

In particular, FIG. 4 shows a variable-TE spiral pulse sequence (FIG. 4A) and spiral interleaves (FIG. 4B) in accordance with embodiments of the present disclosure for 3D UTE imaging. FIG. 4A illustrates a sequence for acquiring a single spiral interleaf, and FIG. 4B illustrates a "stack" of multiple acquired spiral interleaves. FIG. 4A shows one repetition time (TR) of a variable-TE stack-of-spirals pulse sequence in accordance with some embodiments of the present disclosure. A hard RF pulse, represented by the top line, begins the sequence of events. The required partition-encoding gradient, called Gz on the second line, is played out immediately thereafter. The gradient is designed to meet the necessary area in as short a time as possible in order to minimize all echo times. Conventionally, all readout events would be aligned in time (i.e., have the same time delay, or echo time, after the RF pulse), but in this method, the spiral readout (Gx) begins as soon as possible after Gz is complete for the given partition. As Gz is incremented to encode further reaches of k-space, Gx must be incrementally delayed, represented by the Gx subscripts. For the center of k-space ($k_0$), the minimum achievable TE can be very short. The maximum extent in k-space is user-selectable ($k_N$), and will have the longest TE.

Figure 5:
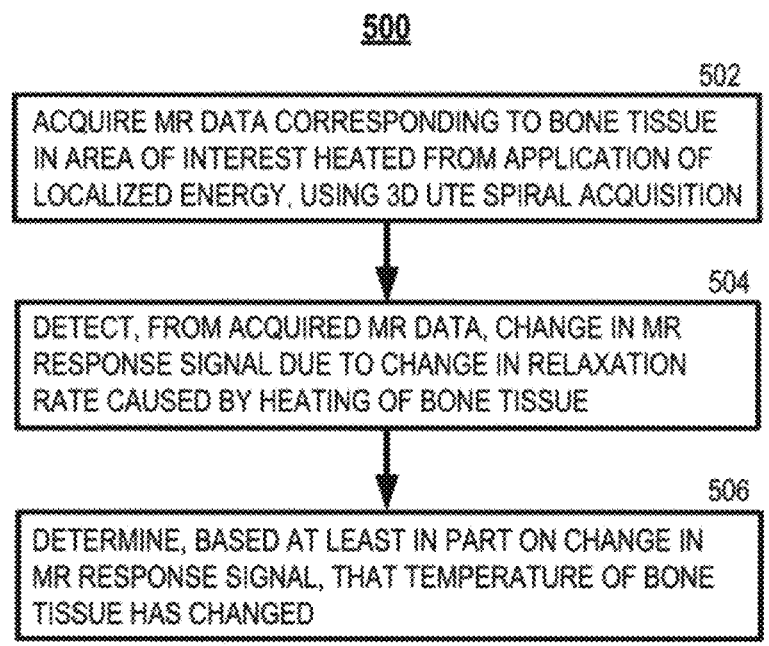
FIG. 5 is a flow diagram illustrating a method in accordance with one embodiment of the present disclosure.

FIG. 5 is a flow diagram illustrating a method in accordance with an embodiment of the present disclosure. As shown, the method 500 includes the step 502 of acquiring magnetic resonance (MR) data corresponding to bone tissue in an area of interest of a subject that is heated from the application of localized energy. The area of interest can include the head of the subject and the bone tissue can correspond to at least a part of the skull of the subject. The localized energy can be from the application of focused ultrasound (FUS).

The acquiring step 502 includes applying a three-dimensional (3D) ultra-short echo time (UTE) spiral acquisition sequence. The method 500 also includes the step 504 of detecting, from the acquired magnetic resonance data, a change in MR response signal due to a change in at least one relaxation rate and/or change in magnetization density caused by heating of the bone tissue. The change in relaxation rate(s) can be a change in a T1 relaxation rate and/or T2 relaxation rate. The method 500 further includes the step 506 of determining, based at least in part on the change in the MR response signal, that the temperature of the bone tissue has changed.

In step 502, applying the 3D UTE spiral acquisition sequence can include applying a variable echo time (TE) 3D stack-of-spirals acquisition sequence with a nonselective excitation pulse. The method 500 may also include a step of measuring, based at least in part on the change in the MR response signal, the temperature of the bone tissue and/or the change in temperature of the bone tissue.

In step 504, detecting the change in MR response signal can include detecting a decrease in the MR response signal due to an increase in T1 relaxation time caused by heating of the bone tissue, and in step 506, determining that the temperature of the bone tissue has changed can include associating the decrease in the MR response signal with an increase in temperature of the bone tissue.

In step 506, in one embodiment, determining that the temperature of the bone tissue has changed can include associating the decrease in the MR response signal with an increase in temperature of the bone tissue. Determining that the temperature of the bone tissue has changed (step 506) can also include comparing at least one characteristic of the MR response signal corresponding to the heated bone tissue to a corresponding at least one characteristic of a reference MR response signal corresponding to the bone tissue at a known temperature. The step 506 of detecting the change in the MR response signal can be performed during application of the localized energy.

The acquired magnetic resonance data can include imaging data for reconstructing images of the area of interest, and the step 506 of determining that the temperature of the bone tissue has changed can be based at least in part on the imaging data. The method 500 may also include reconstructing images of the area of interest from the imaging data, where at least one of the reconstructed images includes a visual representation of the bone tissue heated from the application of the localized energy. The reconstructed image(s) including the visual representation of the bone tissue can be generated by a weighted subtraction of imaging data corresponding to the area of interest at a late TE from imaging data corresponding to the area of interest at approximately the minimum TE. The reconstructed image(s) including the visual representation of the bone tissue can be reconstructed based on imaging data corresponding to approximately the minimum TE. The minimum TE can be about 50 µs.

EXAMPLE IMPLEMENTATIONS AND RESULTS

Various aspects of the present disclosure will now be described with reference to some example implementations and corresponding results and the illustrations of FIGS. 6-10. Some experimental data are presented herein for purposes of illustration and should not be construed as limiting the scope of the present disclosure in any way or excluding any alternative or additional embodiments.

Example 1

Methods

In one example implementation, a 3D spiral UTE sequence was used for rapid UTE imaging of an ex vivo bovine tibia (bone sample). In a first test, a room-temperature bone sample was placed into the bore of an MRI system (Avanto, Siemens) and a spiral UTE sequence was used to acquire volumetric images every 75 seconds for 12.6 minutes. Parameters for imaging were: TR=11.6 ms; two echoes were collected, $TE_{min}$=50-370 µs, $TE_{late}$=9.58-9.61 ms; flip angle=28°; matrix 96×96×16; 203 linear variable density interleaves of 0.4 ms duration each (sampling density decreased from 1.0 at the center of k-space to 0.7 at the edge); 2 averages; a body array coil in a 1.5 T scanner (Avanto, Siemens) was used. Following this acquisition, the bone was placed into a 55° C. water bath for 5 minutes, then imaged again with the same protocol. FIG. 6 shows obtained spiral UTE images of the bone sample, and where FIG. 6A corresponds to minimum TE, FIG. 6B corresponds to a late TE, and FIG. 6C is a subtraction image, highlighting cortical bone. As illustrated, cortical bone is only detectable when using the minimum TE configuration.

A second test was performed using only a heated bone sample in a water bath, using thermocouples to monitor temperature. In this test, there were a few deviations from the above-described, first test protocol, namely: $TE_{late}$=5 ms, flip angle=40°, $N_{partitions}$=32, spiral readout duration=0.8 ms, 1 average. After imaging, the bone was manually segmented and the mean signal intensity was recorded at each time point.

Results

Figure 7A:
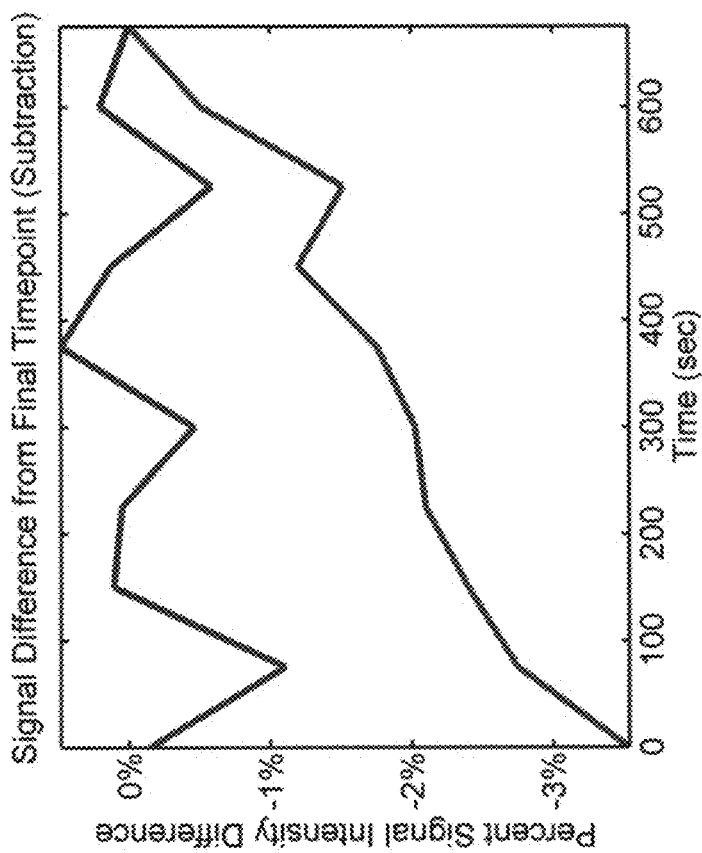
FIGS. 7A and 7B show the mean signal difference of a bone sample, referenced from a final time point, associated with one implementation of the present disclosure, and corresponding results.
Figure 7B:
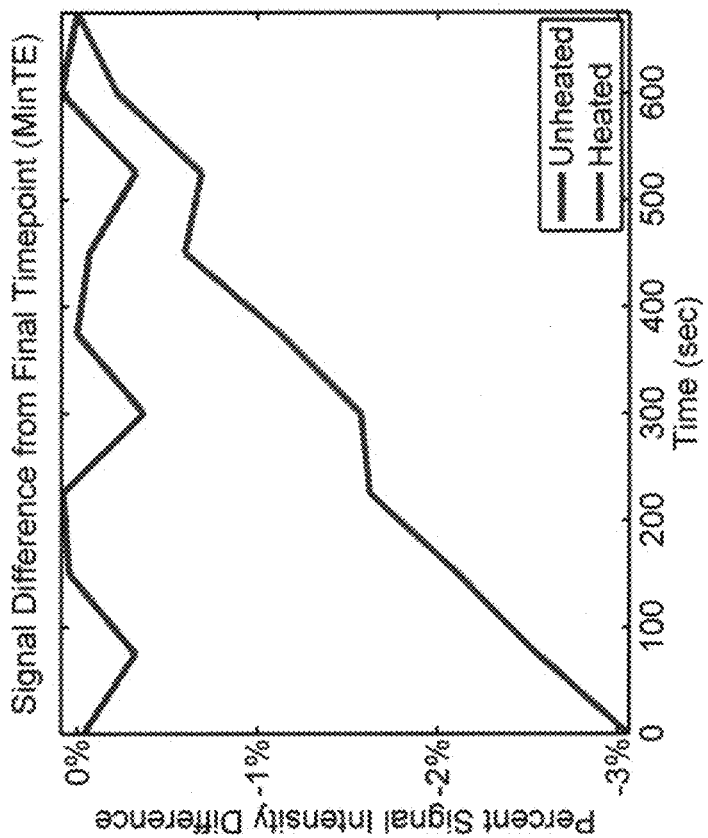

FIGS. 7A and 7B show the mean signal difference of the bone sample, referenced from a final time point, for the first test described above. The graph of FIG. 7A was generated from data corresponding to $TE_{min}$ images and illustrates plots of the percent signal intensity difference (i.e., signal intensity difference of the MR response signal) over time for both the heated sample and unheated sample. The graph of FIG. 7B was generated from data corresponding to subtraction images from subtracting $T_{late}$ images from $TE_{min}$ images, and illustrates plots of the percent signal intensity difference over time for both the heated sample and unheated sample.

As can be seen, the mean signal of the heated sample ("heated") increases as the bone cools (in the bore of the magnet) over a 12-minute time span. In contrast, the sample that remained at room temperature ("unheated") shows no change in signal. As shown in the graph of FIG. 7B, a similar trend is observed with data generated by subtracting $TE_{late}$ images from $TE_{min}$ images.

Figures 8A, 8B:
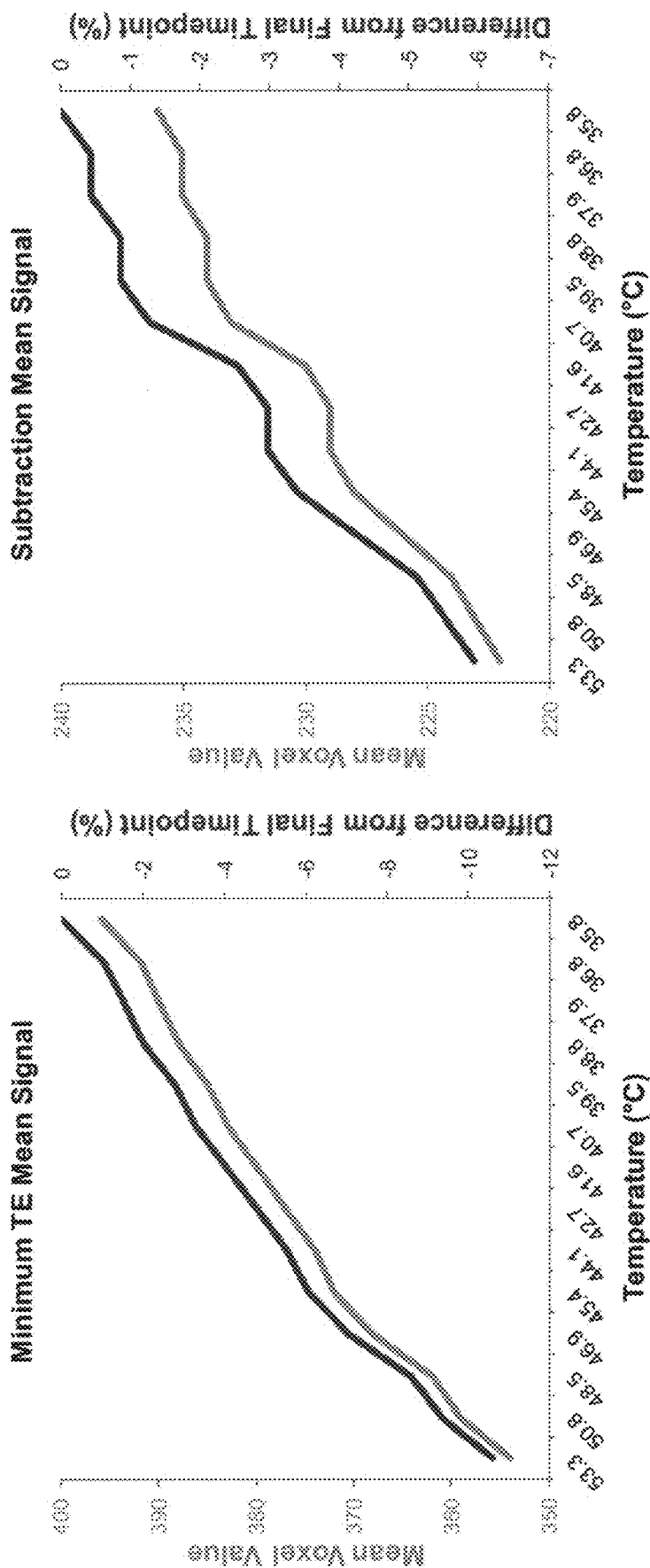
FIGS. 8A and 8B show the mean signal difference of a bone sample, referenced from a final time point, associated with another implementation of the present disclosure, and corresponding results.

FIGS. 8A and 8B illustrate the mean signal difference, referenced from a final time point, of the bone sample and setup for the second test described above. In both of these Figures, the same trend of increasing signal over time is observed in all data generated from $TE_{min}$ images (FIG. 8A) and subtraction images (FIG. 8B). As shown, the minimum $T_E$ mean signal (FIG. 8A) and subtraction mean signal (FIG. 8B) are each represented with plots showing relationships between temperature of the sample and corresponding mean voxel values based on the image data (as well as percentage difference from the final timepoint).

Example 2

Methods

In one example implementation, a 3D spiral UTE sequence corresponding to the 3D spiral UTE sequence shown and described with reference to FIGS. 4A and 4B above, was used for whole-head skull imaging using a human volunteer.

A 60 µs nonselective hard RF excitation pulse (rectangular RF waveform) was used, reducing the minimum TE to 50 µs. Maximum TE depended on number of slices and slice resolution, and was generally in the range of 250-400 µs.

Figure 9:
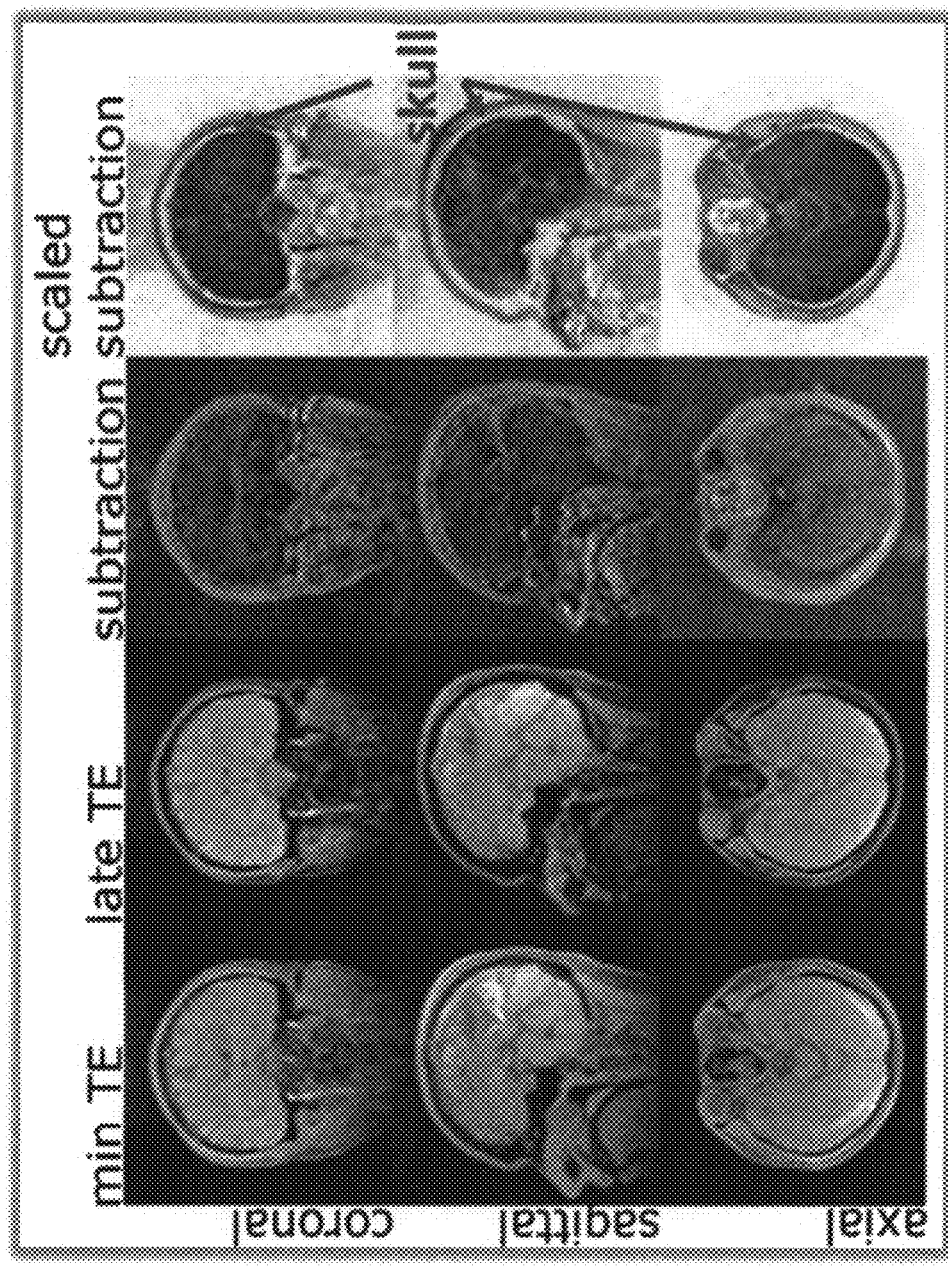
FIG. 9 shows whole-head UTE images obtained by implementing aspects of the present disclosure in accordance with some embodiments.
Figure 10:
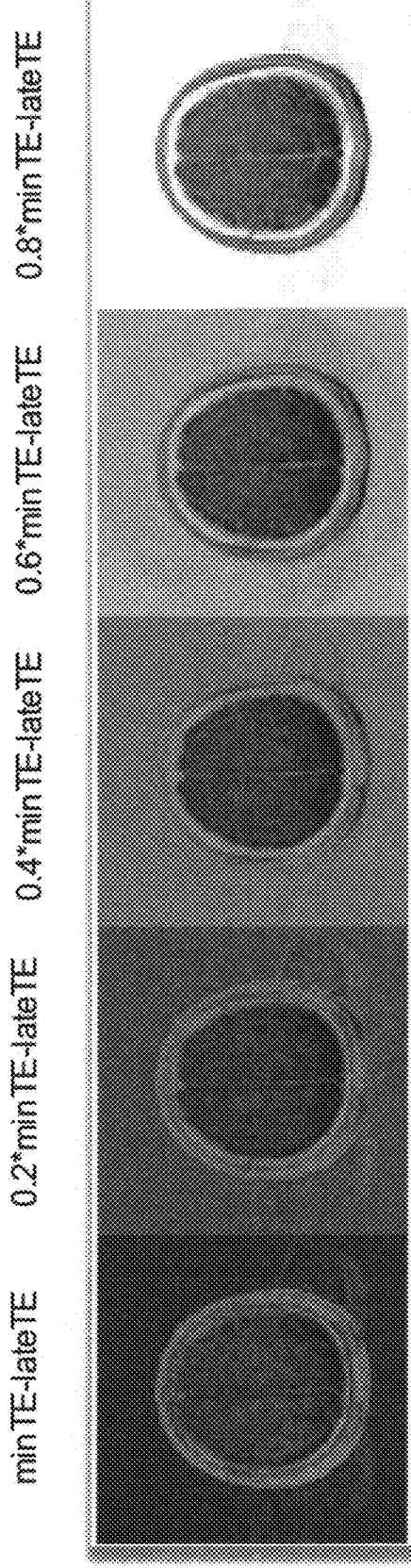
FIG. 10 shows scaled subtraction images associated with the UTE images of FIG. 9.

A whole human skull was scanned with the following parameters: TR=10 ms; TE=50-370 µs; flip angle 5°; matrix 96×96×64; FOV 240 mm³; 98 interleaves of 1.0 ms duration each; 2 echoes, minTE and lateTE (5.1 ms); 67-second acquisition time. Imaging was performed using a 12-channel head RF coil. A second volumetric image was obtained with a TE of 5.1 ms (to preserve fat/water phase) to provide late-TE comparison images. Two echoes were acquired and they were subtracted to highlight the bone signal. FIG. 9 shows whole-head spiral UTE images alongside late-echo images to illustrate the difference in contrast achievable with UTE imaging sequences described above in accordance with embodiments of the present disclosure. Direct subtractions (see "subtraction" column of images in FIG. 9) as well as scaled subtractions (see "scaled subtraction" column of images in FIG. 9 and row of images in FIG. 10) are also shown, highlighting the bone signal.

Results

The above described implementations and results show that whole-head UTE imaging is feasible within short acquisition times.

Among other benefits and advantages of practicing various aspects of the present disclosure in accordance with the above-mentioned example implementations and results for imaging of the whole head of a subject (and with reference to FIGS. 9 and 10), by utilizing nonselective RF pulses, the minimum echo time achievable by a stack-of-spirals UTE sequence can be reduced (from 600 µs to 50 µs in the particular implementations described above), enabling capture of signals from tissues such as bone that have quick signal decay. The efficiency of spiral readouts in accordance with embodiments of the present disclosure supports rapid generation of 3D UTE images, achieving whole-head UTE images in 67s.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is indicated by the appended claims, rather than the foregoing description, and all changes that come within the meaning and range of equivalents thereof are intended to be embraced therein.

What is claimed is:

1. A method, comprising:
  acquiring magnetic resonance (MR) data corresponding to bone tissue in an area of interest of a subject that is heated from the application of localized energy, wherein the acquiring comprises applying a three-dimensional (3D) ultra-short echo time (UTE) spiral acquisition sequence;
  detecting, from the acquired magnetic resonance data, a change in MR response signal due to a change in at least one of relaxation rate and magnetization density caused by heating of the bone tissue; and
  determining, based at least in part on the change in the MR response signal, that the temperature of the bone tissue has changed;

wherein applying the 3D UTE spiral acquisition sequence comprises applying a variable echo time (TE) 3D stack-of-spirals acquisition sequence with a nonselective excitation pulse.

2. The method of claim 1, wherein the change in the MR response signal is due to a change in relaxation rate and the relaxation rate comprises at least one of T1 relaxation rate and T2 relaxation rate.

3. The method of claim 1, further comprising measuring, based at least in part on the change in the MR response signal, at least one of the temperature of the bone tissue and the change in temperature of the bone tissue.

4. The method of claim 1, wherein detecting the change in MR response signal comprises detecting a decrease in the MR response signal due to an increase in T1 relaxation time caused by heating of the bone tissue.

5. The method of claim 4, wherein determining that the temperature of the bone tissue has changed further comprises associating the decrease in the MR response signal with an increase in temperature of the bone tissue.

6. The method of claim 1, wherein determining that the temperature of the bone tissue has changed comprises comparing at least one characteristic of the MR response signal corresponding to the heated bone tissue to a corresponding at least one characteristic of a reference MR response signal corresponding to the bone tissue at a known temperature.

7. The method of claim 1, wherein the localized energy is from the application of focused ultrasound (FUS).

8. The method of claim 1, wherein the detecting of the change in the MR response signal is performed during application of the localized energy.

9. The method of claim 1, wherein the acquired magnetic resonance data comprises imaging data for reconstructing images of the area of interest.

10. The method of claim 9, wherein determining that the temperature of the bone tissue has changed is based at least in part on the imaging data.

11. The method of claim 9, further comprising reconstructing images of the area of interest from the imaging data, wherein at least one of the reconstructed images comprises a visual representation of the bone tissue heated from the application of the localized energy.

12. The method of claim 11, wherein the at least one of the reconstructed images comprising the visual representation of the bone tissue is generated by a weighted subtraction of imaging data corresponding to the area of interest at a late TE from imaging data corresponding to the area of interest at approximately a minimum TE.

13. The method of claim 11, wherein the at least one of the reconstructed images comprising the visual representation of the bone tissue is reconstructed based on imaging data corresponding to approximately a minimum TE.

14. The method of claim 1, wherein a minimum TE is about 50 μs.

15. The method of claim 1, wherein the area of interest comprises the head of the subject and the bone tissue corresponds to at least a part of the skull of the subject.

16. A system, comprising:
a data acquisition device configured to acquire magnetic resonance (MR) data corresponding to bone tissue in an area of interest of a subject that is heated from the application of localized energy, wherein the acquiring comprises applying a three-dimensional (3D) ultra-short echo time (UTE) spiral acquisition sequence; and
one or more processors coupled to the data acquisition device and configured to cause the system to perform functions comprising:
detecting, from the acquired magnetic resonance data, a change in MR response signal due to a change in at least of relaxation rate and magnetization density caused by heating of the bone tissue; and
determining, based at least in part on the change in the MR response signal, that the temperature of the bone tissue has changed;
wherein applying the 3D UTE spiral acquisition sequence comprises applying a variable echo time (TE) 3D stack-of-spirals acquisition sequence with a nonselective excitation pulse.

17. The system of claim 16, wherein the change in the MR response signal is due to a change in relaxation rate and the relaxation rate comprises at least one of T1 relaxation rate and T2 relaxation rate.

18. The system of claim 16, wherein the data acquisition device comprises a magnetic resonance imaging device.

19. The system of claim 16, further comprising a focused ultrasound device (FUS) configured to apply the localized energy.

20. A non-transitory computer-readable medium having stored instructions that, when executed by one or more processors, cause one or more computing devices to perform functions that comprise:
acquiring magnetic resonance (MR) data corresponding to bone tissue in an area of interest of a subject that is heated from the application of localized energy, wherein the acquiring comprises applying a three-dimensional (3D) ultra-short echo time (UTE) spiral acquisition sequence;
detecting, from the acquired magnetic resonance data, a change in MR response signal due to a change in at least one of relaxation rate and magnetization density caused by heating of the bone tissue; and
determining, based at least in part on the change in the MR response signal, that the temperature of the bone tissue has changed;
wherein applying the 3D UTE spiral acquisition sequence comprises applying a variable echo time (TE) 3D stack-of-spirals acquisition sequence with a nonselective excitation pulse.

* * * * *